United States Patent [19]

Fujii et al.

[11] Patent Number: 5,411,535
[45] Date of Patent: May 2, 1995

[54] CARDIAC PACEMAKER USING WIRELESS TRANSMISSION

[75] Inventors: Tadashi Fujii, Fujinomiya; Shinji Ishida, Nakai, both of Japan

[73] Assignee: Terumo Kabushiki Kaisha, Tokyo, Japan

[21] Appl. No.: 25,132

[22] Filed: Mar. 2, 1993

[30] Foreign Application Priority Data

Mar. 3, 1992 [JP] Japan ................. 4-044992

[51] Int. Cl.⁶ .......................................... A61N 1/365
[52] U.S. Cl. ...................... 607/32; 607/37; 607/62; 128/903
[58] Field of Search .............. 607/37, 36, 60, 62, 607/2, 32; 128/903

[56] References Cited

U.S. PATENT DOCUMENTS

| | | | |
|---|---|---|---|
| 3,218,638 | 11/1965 | Honig | 607/60 |
| 3,943,936 | 3/1976 | Rasor et al. | 128/419 |
| 4,844,076 | 7/1989 | Lesho et al. | 128/903 |
| 4,886,064 | 12/1989 | Strandberg | 128/903 |
| 5,012,806 | 5/1991 | De Bellis | 128/903 |
| 5,058,581 | 10/1991 | Silvian | 607/32 |
| 5,095,903 | 3/1992 | De Bellis | 128/903 |
| 5,109,845 | 5/1992 | Yuuchi et al. | 607/60 |

OTHER PUBLICATIONS

Rubenson et al., "Telemetry of electrophysiologic variables from conscious dogs: System design, validation, & serial studies," *American Heart Jour.*, Jan. 1984, pp. 90–96.

*Primary Examiner*—William E. Kamm
*Assistant Examiner*—Kennedy J. Schaetzle
*Attorney, Agent, or Firm*—Burns, Doane, Swecker & Mathis

[57] ABSTRACT

A cardiac pacemaker improved to reduce the weight and size and to unburden the wearer of the pacemaker, while ensuring safe transmission of signals. The cardiac pacemaker includes a cardiac pacemaker main body 100 having at least two electrodes for detecting cardio-information, a control section for performing a control by outputting pulses on the basis of the cardio-information, and a transmitting section for modulating the pulses and transmitting the modulated pulses. The pacemaker also has pacing electrode portion having a receiving section for receiving the transmitted pulses and stimulating electrodes activated by the pulses output from the receiving section.

6 Claims, 8 Drawing Sheets

CARDIAC PACEMAKER USING WIRELESS TRANSMISSION

BACKGROUND OF THE INVENTION

The present invention relates to a cardiac pacemaker and, more particularly, to a cardiac pacemaker which is improved to avoid any feel of constraint of the patient.

A cardiac pacemaker is a device which detects cardiac information and which imparts stimulation to heart based on the cardiac information to control the pacing of the heart. In recent years, improvements have been made in the field of cardiac pacemaker such as reduction in the size and weight of the pacemaker, prolongation of the life of the battery, improvement in the lead electrodes and so forth, as well as novel functions such as a programmable function which enables extra-body adjustment of the pacing conditions and physiological pacing function which can be incorporated in the pacemaker. Thus, nowadays, cardiac pacemaker as an artificial organ has been developed to a considerably high level of perfection. These improvements also permit safe and easy operation for imbedding. It is to be noted, however, a greatest difficulty is encountered in bringing and keeping the lead electrodes with the endocardium. It is very important that the lead electrodes are securely mounted in proper positions. In some cases, a plurality of lead electrodes are mounted in atrium and ventricle. In most cases, it is not easy to demount the lead electrodes once these electrodes are mounted. Thus, the lead wires are often left in the patient's body, in particular in the heart or blood vessel, even after they have become inoperative due to cutting or due to calcification of the ends of the lead electrodes.

FIG. 12 illustrates a known cardiac pacemaker. The cardiac pacemaker 300 has a main body 340, lead wires 350 and lead electrodes 355 for delivering the stimulating pulses to the cardiac muscle. This known cardiac pacemaker, however, suffers from the following disadvantage due to the fact that the main body 340 and the stimulating electrodes 355 are connected through lead lines 350.

First problem

Mal-function of the pacemaker tends to be caused by inferior sealing in the region 320 where the main body 340 is connected to the lead lines. Such inferior sealing is a problem also from the view point of safety in electricity.

Second problem

In order to ensure that the connecting region 320 is sealed without fail, the connecting region 320 inevitably occupies a large portion, e.g., ¼ or so in volume, which seriously impedes reduction in the weight and size of the main body 340.

Third problem

In some cases, the lead lines 350 are too long to fit on the patient's body. Any surplus portion of the lead lines 350 is wound on the main body 340. Consequently, it is necessary to preserve, in the thorax, a space of a volume greater than that required for imbedding the main body 340.

Fourth problem

Problems are still encountered that the risk of pacing failure due to cutting of the lead line 350 and difficulty in taking the inoperative lead lines out of the patient's body.

Fifth problem

Blocking in a blood vessel or pressurizing of the blood vessel may dangerously occur particularly when the patient is an aged person.

SUMMARY OF THE INVENTION

In view of these problems of the known art, it is an object of the present invention to provide a cardiac pacemaker in which the cardiac pacing is controlled by wireless transmission of the stimulating signals from the pacing electrodes from the main body of the pacemaker, thus eliminating necessity for the lead lines which are used in known cardiac pacemakers.

To this end, according to the present invention, there is provided a cardiac pacemaker, comprising: a cardiac pacemaker main body including, at least two detecting means for detecting cardio-information, control means for outputting controlled pulse on the basis of the cardio-information, and transmission means for modulating and transmitting the pulses; receiving means for receiving and demodulating the transmitted pulses; and stimulating electrode means which is activated by output pulses from the receiving means.

Thus, in the cardiac pacemaker of the present invention, the main body of the pacemaker and the pacing electrodes are physically independent from each other, and transmission of the signals from the main body to the pacing electrodes is conducted in a wireless manner. Consequently, the hermetic sealing structure for sealing the pacemaker main body can easily be formed, contributing to reduction in the size and weight of the pacemaker. In addition, the necessity for lead lines is eliminated, so that problems such as mal-function due to cutting of the lead lines and blocking in the blood vessel, as well as pressing of the same, is avoided, and imbedding of the pacemaker is facilitated. In addition, it is required only to imbed the pacing electrodes, so that the volume to be preserved in the patient's body is minimized to unburden the patient.

Preferably, the cardiac pacemaker is composed of two parts: namely, a cardio-information detecting section which includes at least two electrodes for detecting cardio-information and a transmitting section for modulating and transmitting the cardio-information; and a pacemaker main body having a receiving section for receiving and demodulating the cardio-information transmitted from the transmitting section, a control section for performing a control by outputting pulses on the basis of the cardio-information received by the receiving section, and a transmitting section for modulating the pulses and transmitting the modulated pulses. When such an arrangement is adopted, the portion from which the cardio-information is derived can be freely determined, by virtue of the fact that the cardiac information detecting section and the pacemaker main body are separate from each other. Consequently, it is possible to provide the cardio-information detecting section on the endocardium, without attaching the pacemaker main body, so that cardio-information can be directly derived from the endocardium.

The positions where the pacing electrodes and the cardio-information detecting section are fixed to the endocardium varies according to the state of the patient: namely, the pacing electrodes and the cardio-information detecting section may be fixed both to the ventricle and the atrium; the pacing electrode may be fixed to only one of the atrium and ventricle; or the cardio-information detecting section and the pacing electrode are fixed to the ventricle and the atrium, respectively.

It is possible to employ two or more pacing electrodes, while using electromagnetic waves as the transmitted pulse signals. In such a case, different frequencies are employed for these two pacing electrodes, thus preventing interference or mixing of the signals. It is also possible to use the same frequency for both pacing electrodes, in a time-sharing manner. It is also possible to use supersonic signal as the pulse signal. In such a case, it is necessary to provide a piezoelectric transducer between the transmitting section and the receiving section. In this case, however, an advantage is obtained in that the modulation of the signal, which is essentially required when electromagnetic wave is used, is dispensed with. In such a case, the supersonic wave transmitted from the transmitting section is converted into voltage by the piezoelectric transducer in the receiving section and is applied to the electrode section after amplification, thereby stimulating the cardiac muscle. Preferably, the nature of the pulse signal is optimized for the wearer of the pacemaker.

The cardiac pacemaker of the present invention can be used also when a pacing is to be executed in accordance with a physiological change in the patient's body. In such a case, a sensor for measuring the temperature and blood pressure is attached to the wearer's body, and information is transmitted from this sensor to the pacemaker main body, thus enabling pacemaking operation to be conducted in accordance with the information.

The above and other objects, features and advantages of the present invention will become clear from the following description of the preferred embodiment taken in conjunction with the accompanying drawings.

DESCRIPTION OF THE PREFERRED EMBODIMENTS

Figure 1:
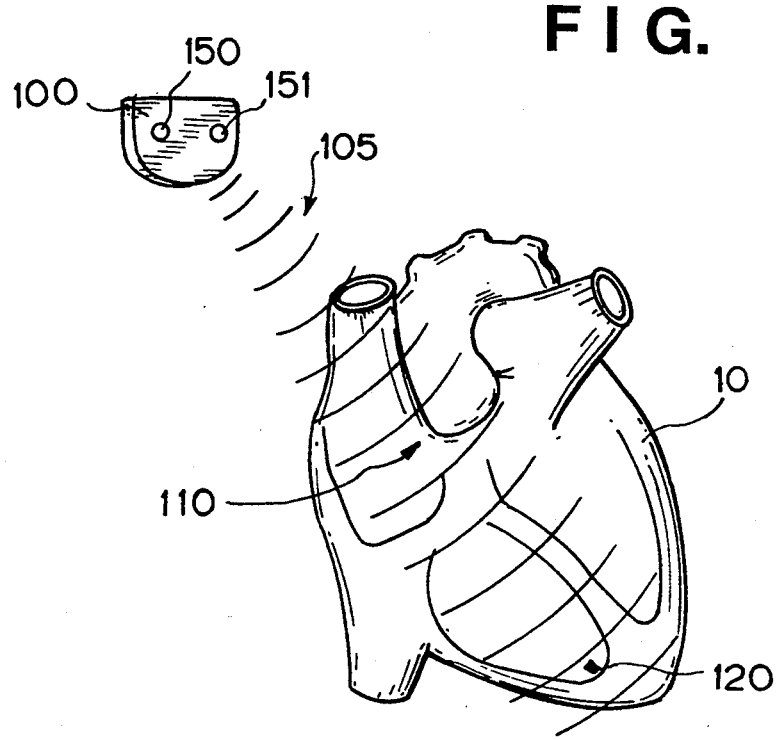
FIG. 1 is an illustration of the concept of a first embodiment of the cardiac pacemaker of the present invention.

<Method of Fixing Pacing Electrode in First Embodiment>

Fixing of the pacing electrode in the patient's body is conducted by mounting the pacing electrode on the end of a catheter, introducing the pacing electrode to a predetermined position in the heart, fixing the pacing electrode to the endocardium, and then extracting only the catheter. This method will be described in more detail with reference to FIGS. 9, 10, 11A and 11B.

The pacing electrode, denoted by 420, has a cylindrical form with a cavity 411. A portion of the wall defining the cavity 411 is threaded as at 402. The cavity 411 receives a screw 401 for fixing the pacing electrode 420. The screw 401 includes an auger or coiled portion 412 having a keenly sharpened end, a screw portion 413 which engages with the thread 402 and a rod-shaped connecting portion 414. The end 404a of the connecting portion 414 is provided with a recess 404b for connection to a later-mentioned screw handle 405. The rod-shaped connecting portion 414 projects from the pacing electrode 420 before the latter is fixed. An "O" ring for fixing the connecting portion 414 is mounted in an opening 415 of the cavity 411. The arrangement is such that, when the screw 401 is driven, the coiled portion 412 projects beyond the opening 415 of the electrode portion 424 of the pacing electrode 420, while rotating about its axis, due to the screwing engagement between the screw portion 413 and the thread 402. A anchoring member 127 is provided around the pacing electrode 420.

A catheter 410 for introducing the pacing electrode 420 to the predetermined position is provided at its one end with a pacing electrode connecting portion 418 and at its other end with an operating portion 419. The catheter 410 is provided therein with an internal lumen 417 and the lumen 417 receives a hollow screw handle 405. The screw handle 405 is provided at its one end with a connecting portion 403a for connection to the aforementioned end 404a of the connecting portion 414. The connecting portion 403a has a projection 403b for mating with the recess 404b, as will be seen from FIGS. 11A and 11B.

The pacing electrode connecting portion 418 has an opening 421 of the lumen 417. The catheter 410 and the pacing electrode 420 are coupled to each other, as the portion of the rod-shaped connecting portion 414 projecting from the pacing electrode 420 is received in the opening 421. The connecting surfaces 427a and 427b are provided with mating recess and projection 423, 424. A hall portion 422 is formed inside the opening 421 of the pacing electrode connecting portion 418. The connecting portion 403a of the screw handle 405 and the connecting portion 404a of the screw 401 fit each other within the hall portion 422. A circumferential rib 408 is provided on the connecting portion 403a of the screw handle 405. The rib 408 is sized to engage with the rear end 409 of the hall portion 422. A stylet 406 is received in the hollow of the screw handle 405.

The fixing of the pacing electrode is conducted in the following manner. The catheter 410 has a fixed form. Thus, the catheter is extended in a substantially straightened form as the stylet 406 is inserted, but resumes its original curved form when the stylet 406 is withdrawn. Using this nature, the end of the catheter is introduced into the heat through a sub-clavian vein and its branch, with the aid of an introducer. The catheter 410 may be formed of a material which does not transmits X-ray, so that the operator can control the advance of the catheter while visually checking the position of the end of the catheter. Consequently, the pacing electrode 420 connected to the end of the catheter is introduced into the heart. When the pacing electrode 420 has reached the aimed position, the electrode portion 424 of the pacing electrode 420 is pressed against the aimed portion of the endocardium and, after the catheter is fixed against rotation, the screw handle 405 is pressed and rotated so that the connecting portion 403a of the screw handle 405 and the connecting portion 414 of the screw 401 are brought into engagement with each other within the hall portion 422. Consequently, the torque of the screw handle 405 is transmitted to the screw 401, so that the screw 401 rotates to progressively drive the coiled portion 412 into the heart 10, thereby fixing the latter. Relative rotation between the pacing electrode 420 and the catheter 410 is prevented because of mating recess and projection 423, 424 at the connecting surfaces 427a, 427b. The length of the portion of the rod-shaped connecting portion 414 projecting from the pacing electrode 420 is reduced by the amount by which the coiled portion 412 of the screw 401 projects from the electrode portion 424.

The anchoring member 127 provided on the pacing electrode 420 entangles with the internal muscle so as to be anchored on the heart. Then, as the stylet 406 is further urged, the opening portion 421 of the catheter 410 is disconnected from the portion of the rod-like connecting portion 414 projecting from the pacing electrode 420, whereby the pacing electrode 420 and the catheter 410 are separated from each other.

Consequently, the pacing electrode 420 is securely fixed to the endocardium both by the screw 401 and the anchoring member 127.

To enable determination of the position where the pacing electrode 420 is fixed, the screw 401 and the stylet 406 are made of electrically conductive materials, and the screw 401 and the stylet 406 made of such materials are pressed onto the endocardium and measurement is conducted in accordance with the known method to find threshold value for the pacing, thus determining the positions where the measured value does not exceed the predetermined value.

<Construction of the Cardiac Pacemaker of This Embodiment>

FIG. 1 schematically shows a first embodiment of the present invention.

The cardiac pacemaker has a main body 100 imbedded in the thorax, an atrium pacing electrode 110 secured to the atrium of the heart 10, and a ventricle pacing electrode 120 secured to the ventricle of the heart 10. The main body 100 and the pacing electrodes 110, 120 are connected to each other in a wireless manner.

As to the wireless manner, communication can be performed using an electric wave or a supersonic wave. In the communication using electric wave, the frequency band of tens MHz to several GHz is applicable.

The main body 100 of the cardiac pacemaker is provided with a pair of cardio-measuring electrodes 150, 151 for the purpose of detecting cardio-information of the wearer, and the main body of the pacemaker transmits signals to the respective pacing electrodes on the basis of the detected cardio-information.

Figure 2:
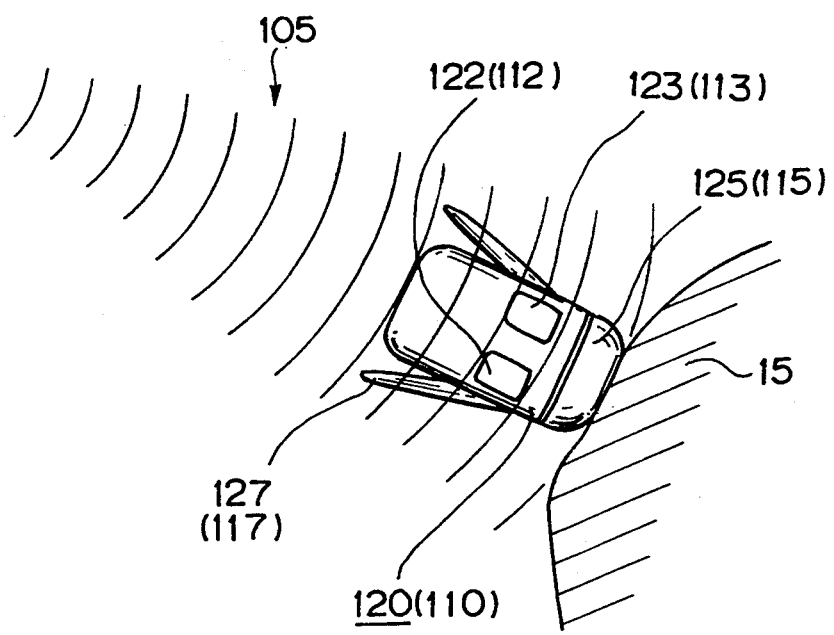
FIG. 2 is an illustration of a state in which a pacing electrode is fixed to an endocardium.

FIG. 2 illustrates the pacing electrode 120 fixed to the endocardium 15. The pacing electrode 120 includes a receiving portion 122 for receiving signal wave transmitted from the main body 100, a demodulating portion 123, and an electrode portion 125 for stimulating the endocardium. The pacing electrode 120 also is provided with an anchoring member 127 for anchoring the pacing electrode 120 to the endocardium. The pacing electrode 110 fixed to the atrium has the similar construction and has components which are denoted by the reference numerals 112 to 117.

Figure 3:
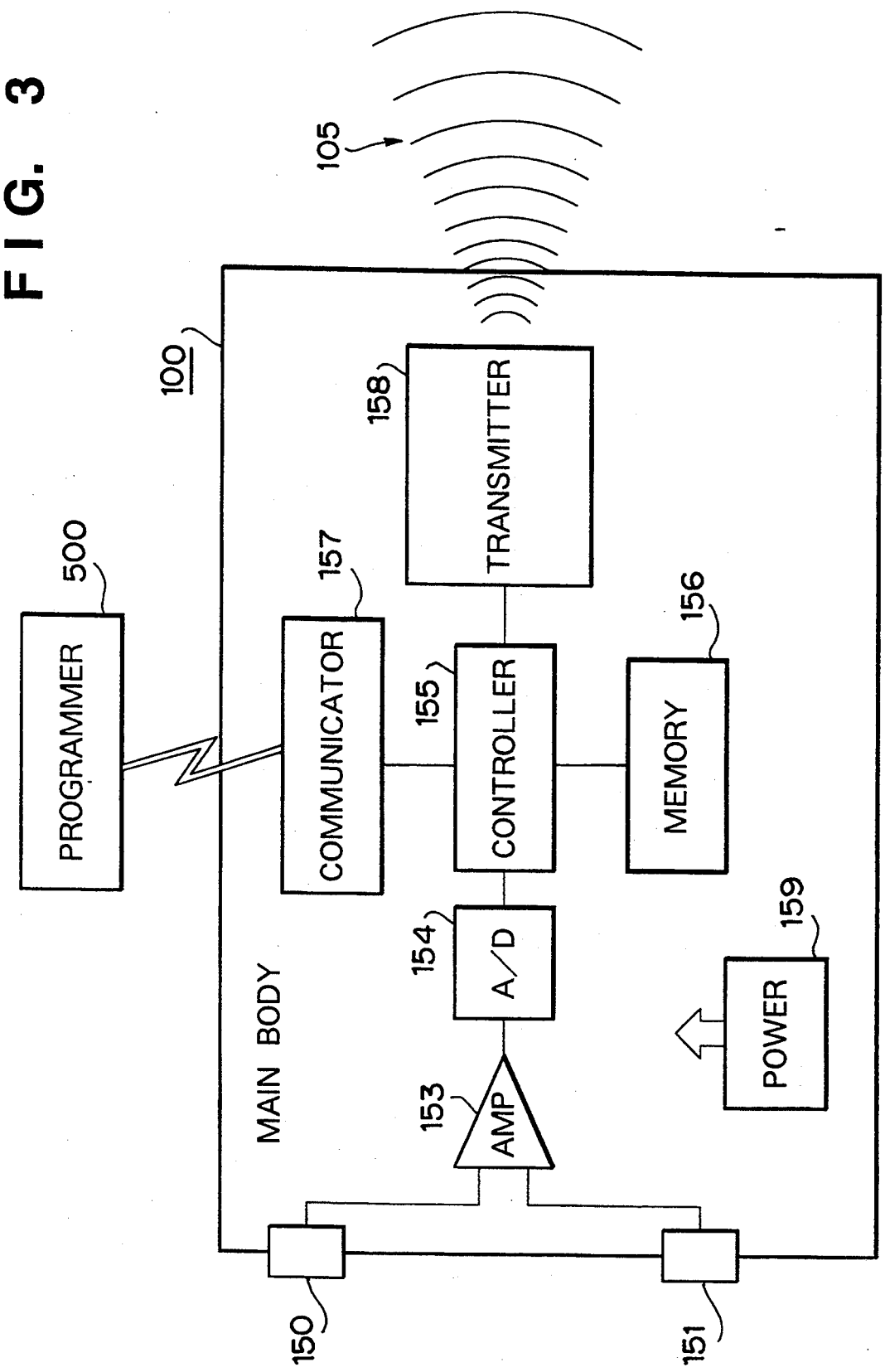
FIG. 3 is a block diagram of a main body of the first embodiment of the cardiac pacemaker.

A detailed description will now be given of the circuit construction of this embodiment, with reference to FIG. 3 which is a block diagram of the main body 100. The pacemaker main body 100 has cardio-measurement electrodes 150, 151, amplifier section 153, A/D converter 154, control section 155, memory section 156, communicating section 157, transmission section 158 and a power supply 159. A signal waveform entered through the measuring electrodes 150, 151 is amplified by the amplifier section 153, and is input to the control section 155 through the A/D converter 154. The control section 155 forms a timing pulse for cardiac pacemaking on the basis of the input cardio-information and the pacing program which is stored in the memory section 156. The timing pulse thus formed is converted into a predetermined transmission wave 105 by the transmission section 158 and is transmitted by the latter. The communication section 157 is used for communication with the externally provided programmer 500 and is used when the pacing program stored in the memory section 156 is to be updated. A pacing program optimum for the patient can be set up by a programmer 500 and is stored in the memory section 157. The pacing program can be altered as desired. The power supply 159 supplied electrical power to respective portions of the pacemaker main body 100.

Figure 4:
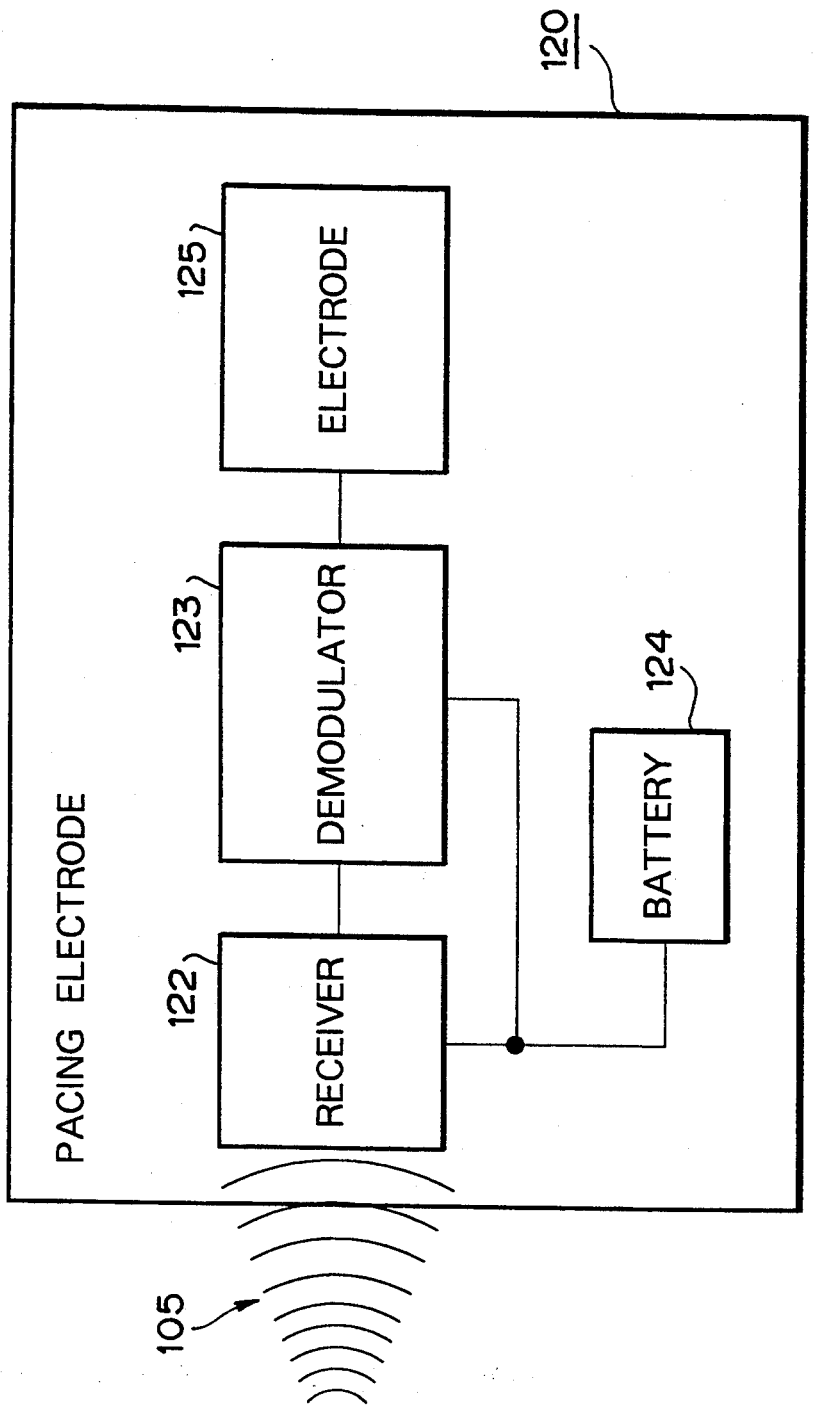
FIG. 4 is a block diagram of a pacing electrode incorporated in the fist embodiment.

FIG. 4 is a block diagram of the pacing electrode 120. The construction of the other pacing electrode 110 will not be described in detail because its construction is the same as that of the pacing electrode 120 which will be described later. The pacing electrode 120 has a receiving section 122, a demodulating section 123, an electrode section 125 and a battery 124. The transmission wave transmitted from the main body is received by the receiving section 122 and the received waveform is supplied to the demodulating section 123 which conducts energy conversion into voltage which is applied to the electrode portion 125. The battery section 124 supplies electrical power both to the receiving section 122 and the demodulating section 123.

This embodiment employs an electromagnetic wave as the transmission wave 105. In order to avoid interference or mixing, waves of different signals are employed for transmission to these two pacing electrodes 110, 120.

Figure 5:
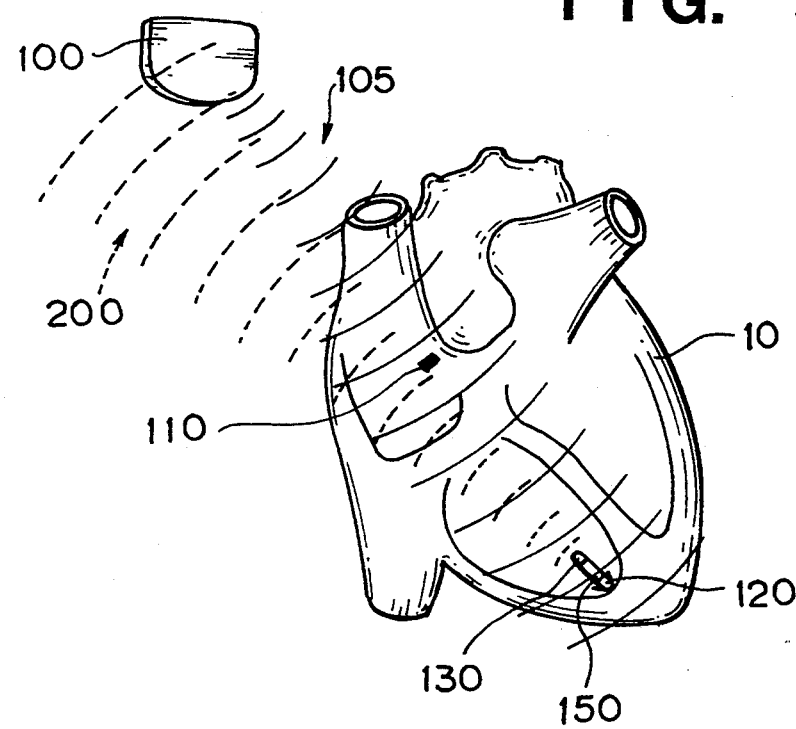
FIG. 5 is an illustration of the concept of a second embodiment of the present invention.

A description will now be given of a second embodiment of the present invention. Referring to FIG. 5 showing the second embodiment, an electrode unit 150, which integrates the cardio-measurement electrode 130 and the pacing electrode 120, is fixed to the endocardium of the ventricle of the heart, while a pacing electrode 110 is fixed to the atrium. The cardio-measurement electrode section 130 transmits cardio-information signal 200 to the main body 100 of the pacemaker. The pacemaker main body 100, imbedded in the thorax, transmits pulse signals to the respective pacing electrodes 110, 120 on the basis of the received cardio-information, thus causing the pacing electrodes to stimulate the endocardium in accordance with the pulse signals.

Figure 6:
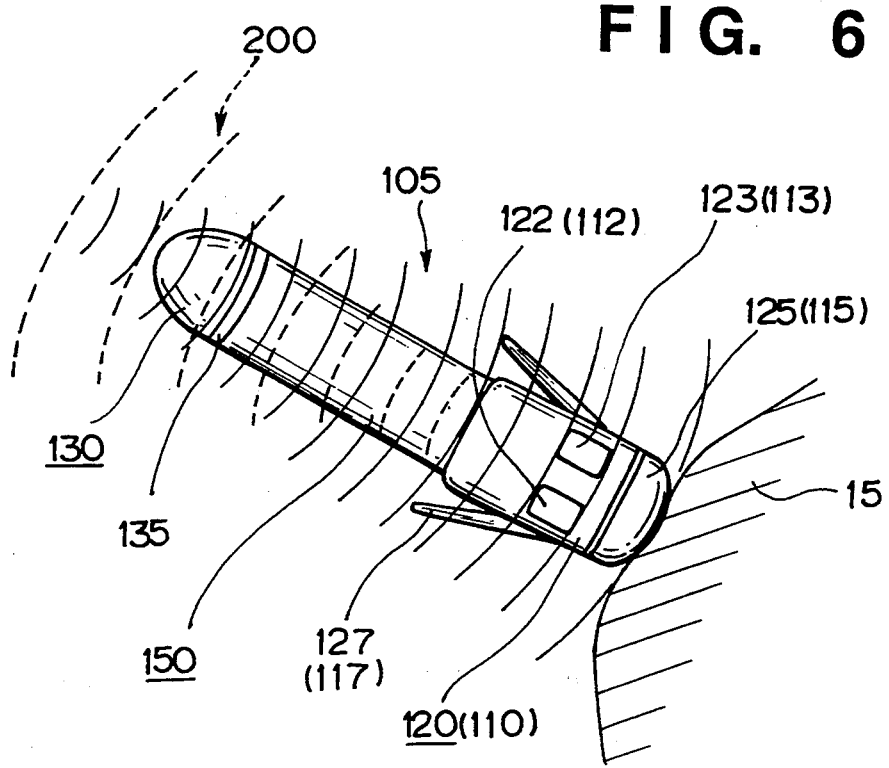
FIG. 6 is an illustration of a state in which an electrode unit used in the second embodiment is fixed to an endocardium.

FIG. 6 shows the state in which the electrode unit 150 is fixed to the endocardium 15. The electrode unit 150 includes a cardio-measuring electrode section 130 and the pacing electrode 120. The pacing electrode section 120 may be of the same type as that used in the first embodiment: namely, it is composed of a receiving section 122 for receiving the pulse signal transmitted from the pacemaker main body 100, a demodulating section 123 and an electrode section 125 for stimulating the cardiac muscle. The pacing electrode section 120 further has an anchoring member 127 for anchoring the electrode section 130 to the endocardium. The cardio-measurement electrode section 130 has cardio-measurement electrodes 135, 125 common to the electrode section of the pacing electrode 120. The cardio-measurement electrodes 135 and 125 are spaced several centimeters from each other. The cardio-information measured between the cardio-measurement electrodes 135 and 125 is transmitted from the electrode unit 150 to the main body 100 of the pacemaker.

Figure 7:
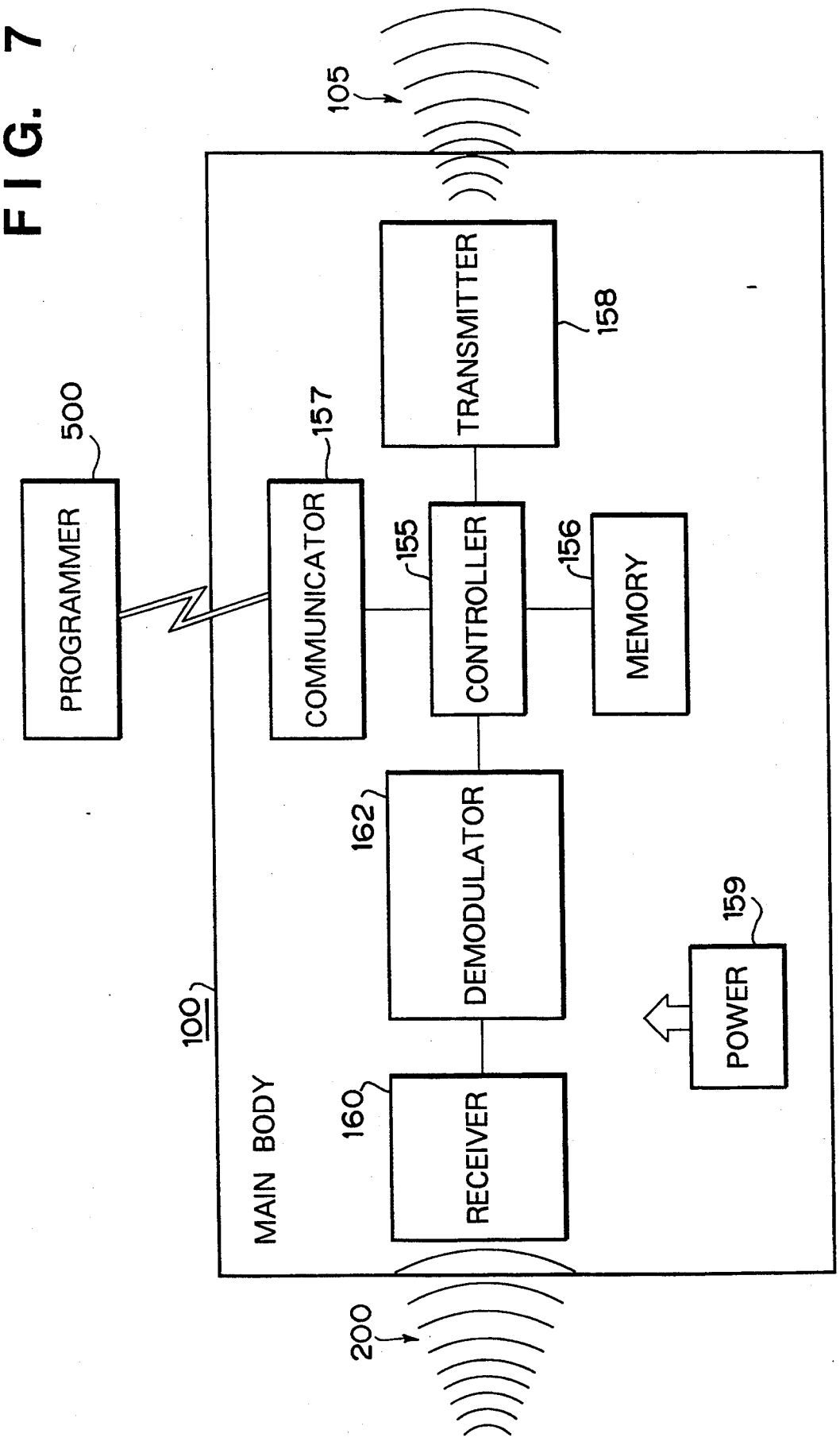
FIG. 7 is a block diagram of the main body of the second embodiment of the cardiac pacemaker.

The operation of this embodiment will be described with reference to FIG. 7 which is a block diagram of the main body 100 of the cardiac pacemaker of this embodiment. The pacemaker main body 100 includes a receiving section 160, a demodulating section 162, a control section 155, a memory section 156, a communicating section 157, a transmission section 158, and a power supply 159. Cardio-information signal received by the receiving section 160 is demodulated by the demodulating section 162 and the demodulated signal is input to the control section 155. The control section 155 produces the timing pulse for cardiac pacemaking on the basis of the cardio-information input thereto and the pacing program which is stored in the memory section 156. The thus generated timing pulse is converted by the transmission section 158 into a predetermined pulse signal 105 and is then transmitted therefrom. The communicating section 157 is used for the communication with an external programmer 500, when the pacing program stored in the memory section 156 is to be updated. It is possible to set a pacing program optimum for individual patients by means of the programmer 500, and to store such optimum pacing program in the memory section 156. The content of the memory can be altered as desired by means of the external pacing programmer. The power supply 159 supplies electrical power to respective portions of the pacemaker 100. In this embodiment, the cardio-measurement electrode has been separated. Other functions are the same as those of the first embodiment and are denoted by the same reference numerals as those used in the explanation of the first embodiment.

Figure 8:
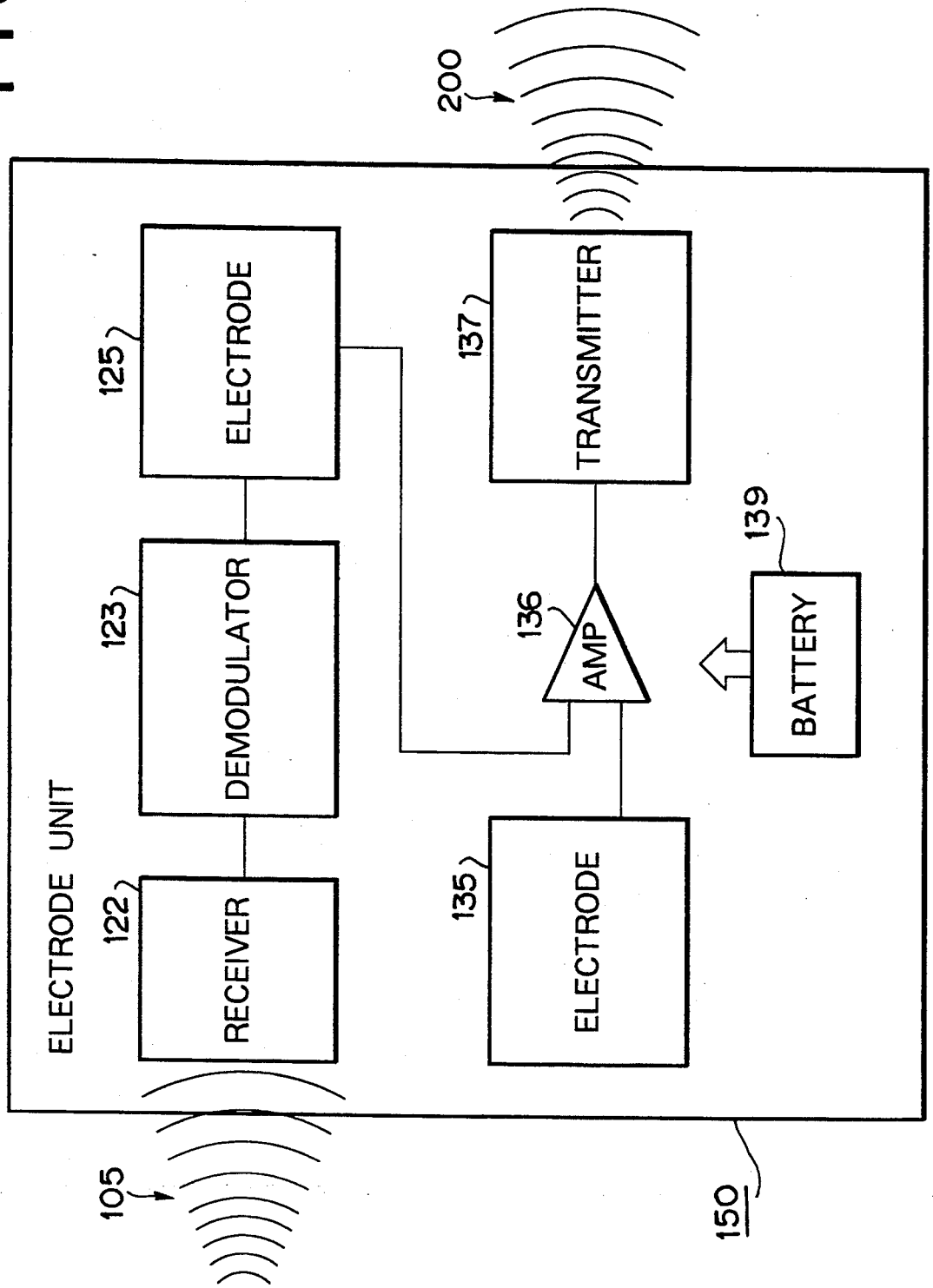
FIG. 8 is a block diagram of the electrode unit used in the second embodiment.
Figure 9:
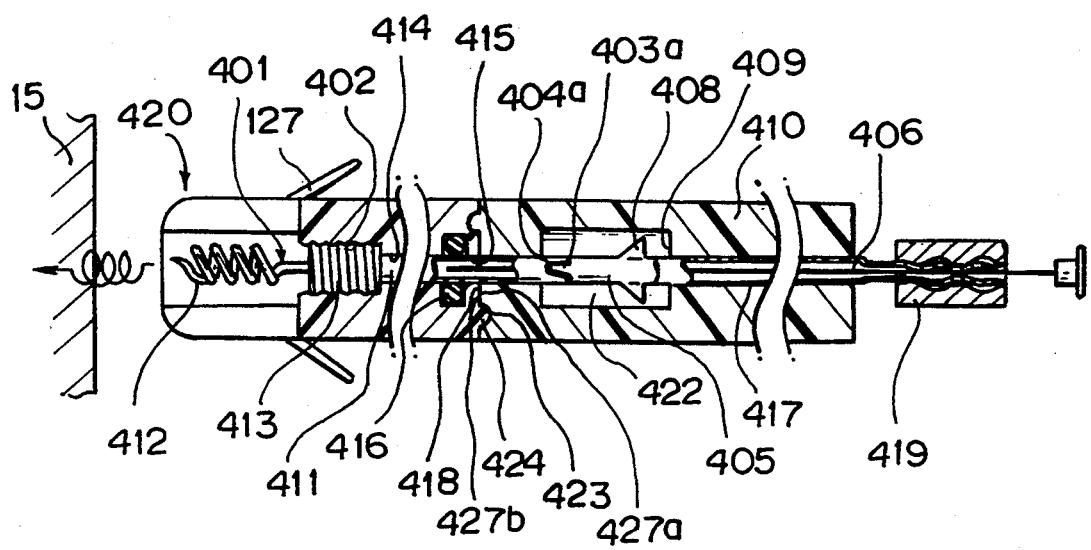
FIG. 9 is an illustration of a state in which a pacing electrode held on the end of a catheter is fixed to an endocardium.
Figure 10:
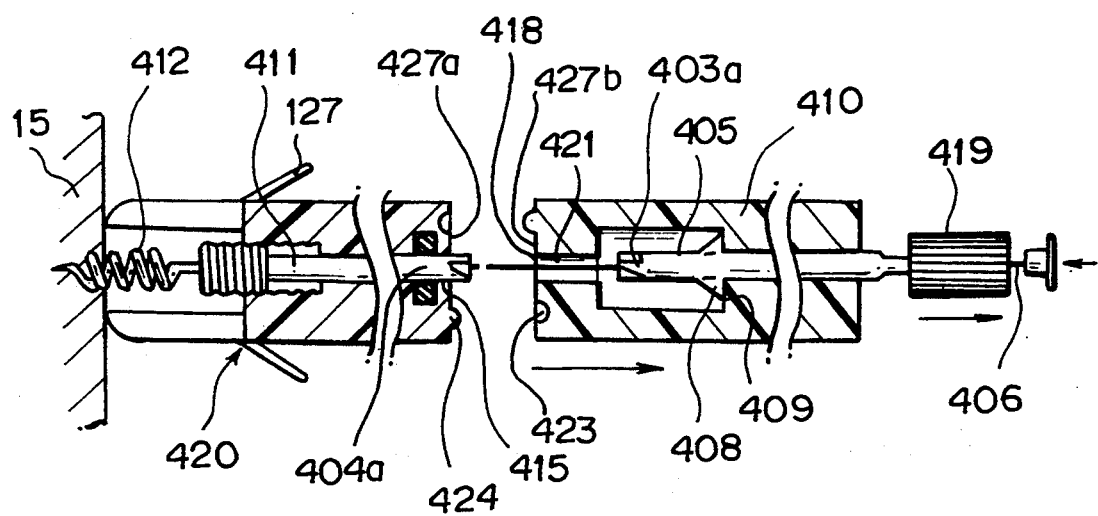
FIG. 10 is an illustration of the state in which the catheter is severed after fixing of the pacing electrode.
Figure 11A:
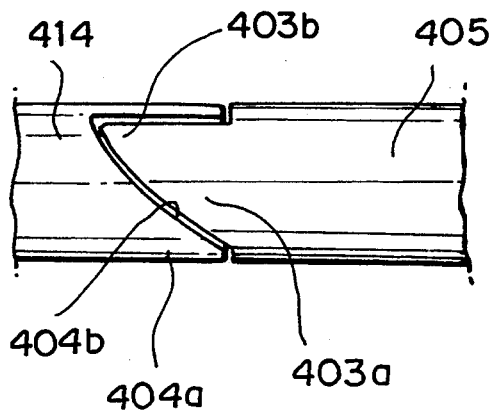
FIGS. 11A and 11B are enlarged views of the joint portion between a screw and a screw handle.
Figure 11B:
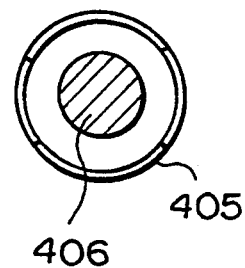
Figure 12:
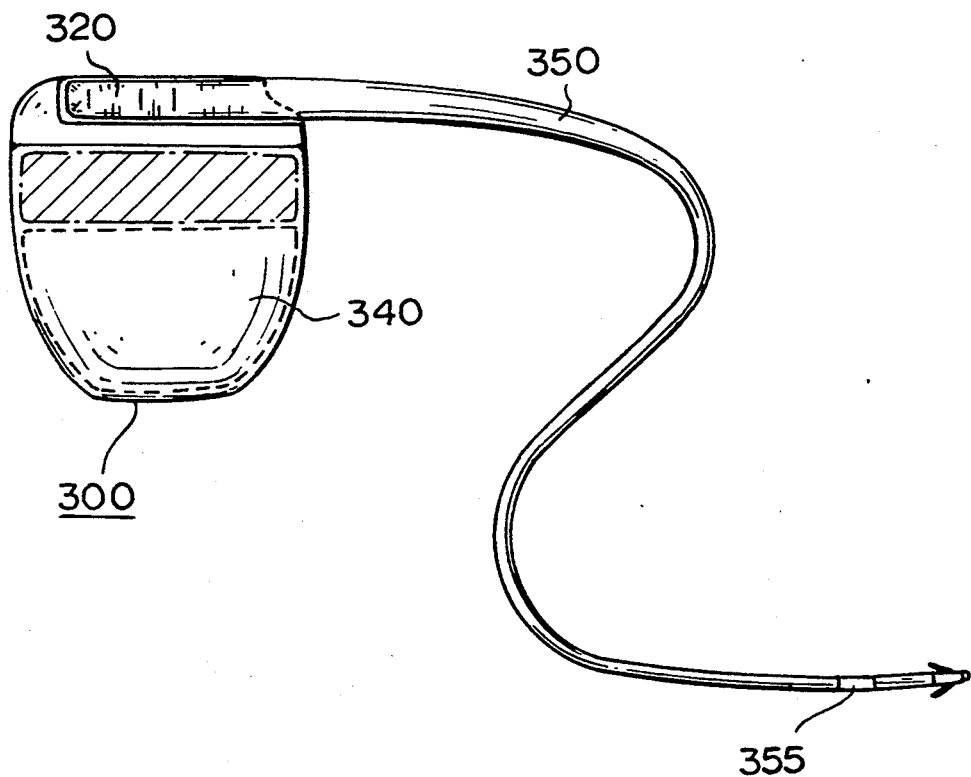
FIG. 12 is an illustration of the known pacemaker.

FIG. 8 is a block diagram of an electrode unit 150. The electrode unit 150 includes a receiving section 122, a demodulating section 123, an electrode section 125 (serves also as cardio-measurement electrode), a cardio-measurement electrode 135, an amplifier section 136, a transmission section 137 and a battery section 139. The cardio-information measured through the cardio-information measuring electrodes 135, 125 is amplified by the amplifier section 136 and is transmitted as cardio-information signal 200 to the pacemaker main body 100 from the transmission section 137. Meanwhile the receiving section 122 receives the transmission wave (pulse signal) 105 transmitted from the pacemaker main body 100 and delivers it to the demodulating section 123. The transmitted wave in the form of pulse signal is then demodulated and amplified by the demodulating section 123 and is supplied to the electrode section 125 as a pacing voltage. The battery section 139 supplies electrical power to various portions of the electrode unit.

In this embodiment, the communicating section 157 and the receiving section 160 are constructed as separate units. The arrangement, however, may be such that a single unit is used both as the communicating section 157 and the receiving section 160 at different frequencies.

According to the present invention, the cardiac pacemaker is composed of a cardiac pacemaker main body including at least two electrodes for detecting cardio-information, a control section for performing a control by outputting a pulse signal on the basis of the cardio-information and a transmitting section for transmitting the pulse signal; and a pacing electrode including a receiving section for receiving and demodulating the transmitted pulse signal and a stimulating electrode activated by the pulse signal output from the receiving section. Thus, the pacemaker main body and the pacing electrode are independent of each other and signal transmission therebetween is conducted in a wireless manner. It is therefore possible to easily obtain hermetic structure of the cardiac pacemaker body, while reducing the size and weight and eliminating necessity for lead lines. Consequently, troubles such as mal-functions due to cutting of the lead lines or impediment to blood vessel are avoided.

In another aspect, the present invention provides a cardiac pacemaker which is composed of a cardio-information detecting section including at least two electrodes for detecting cardio-information and transmitting section for modulating the cardio-information and transmitting the modulated cardio-information; and a pacemaker main body including a receiving section for receiving and demodulating the cardio-information transmitted from the cardio-information detecting section, a control section for performing control by outputting pulses in accordance with the cardio-information, and a transmitting section for modulating the pulses and transmitting the modulated pulses. This arrangement increases the degree of freedom in the selection of the position from which the cardio-information is to be derived. It is therefore possible to provide the cardio-information detecting section on the endocardium, making it possible to directly derive the cardio-information from the endocardium, and to select various arrangements such as provision of the cardio-information detecting section and the pacing electrode on the ventricle and atrium, respectively, according to the state or condition of the patient.

The communication in a wireless manner between the main body 100 and the pacing electrode 120 can be also performed by using supersonic wave. In this case, it is possible to easily transmit supersonic wave by impressing a voltage to a well known piezoelectric material (e.g. lead titanate zirconate, PZT).

At the receiving side, supersonic wave is converted into electric signal (voltage) by using the piezoelectric material. The supersonic wave in the frequency band of MHz order (1–10 MHz) is used preferably, because it is necessary to be well propagated in a body.

Although the invention has been described through its specific forms, it is to be understood that the described embodiments are only illustrative and various changes and modifications may be imparted thereto without departing from the scope of the present invention which is limited solely by the appended claims.

What is claimed is:

1. A cardiac pacemaker comprising:
   a cardiac pacemaker main body including, at least two detecting means for detecting cardio-information, control means for outputting at least one controlled pulse on the basis of the cardio-information, and transmission means for modulating and transmitting the at least one pulse; and
   a pace electrode unit including receiving means for receiving and demodulating the transmitted pulse, and stimulating electrode means which is activated by an output pulse from said receiving means.

2. A cardiac pacemaker comprising:
   a cardio-information detecting unit including, at least two detecting means for detecting cardio-information, and cardio-information transmitting means for modulating the cardio-information and transmitting the modulated information;
   a cardiac pacemaker main body including receiving means for receiving and demodulating the cardio-information transmitted from said cardio-information transmitting means, control means for outputting at least one controlled pulse on the basis of the received cardio-information, and transmission means for modulating the at least one pulse and for transmitting the modulated pulse; and
   a pacing electrode unit including receiving means for receiving and demodulating the modulated pulse transmitted from said pacemaker main body, and stimulating electrode means which is activated by an output pulse from said receiving means.

3. A cardiac pacemaker comprising a cardiac pacemaker main body and a pacing electrode unit,
   said cardiac pacemaker main body including:
   first carrier wave generating means for generating a carrier wave of a first frequency;
   pulse generating means for generating a pulse based on cardio-information;
   transmitting the pulse by using the carrier wave of said first frequency; and
   receiving means for receiving cardio-information carried by a carrier wave of a second frequency different from said first frequency; and
   said pacing electrode unit further including:
   pacing electrode means for receiving the transmitted pulse and giving stimulus corresponding to the transmitted pulse to a ventricle or an atrium wall;
   second carrier wave generating means for generating the carrier wave of said second frequency;
   cardio-information detecting means for detecting cardio-information; and
   transmission means for transmitting the cardio-information carried by the carrier wave of said second frequency.

4. A cardiac pacemaker according to claim 3, wherein said cardiac pacemaker main body includes communication means for performing transmission and receipt at different frequencies.

5. A cardiac pacemaker according to claim 3, further including:
   a catheter to which said pacing electrode unit is detachably secured at a predetermined position in a heart,
   an end of said pacing electrode unit being fixed to a wall of the heart with said catheter being separable from said pacing electrode unit such that said catheter can be withdrawn from said pacing electrode unit.

6. A cardiac pacemaker according to claim 3, wherein said pacing electrode unit includes communication means for performing transmission and receipt at different frequencies.

* * * * *